(12) United States Patent  
Wiechmann

(10) Patent No.: US 8,435,032 B2  
(45) Date of Patent: *May 7, 2013

(54) ORTHODONTIC BRACKET WITH A PAD

(75) Inventor: Dirk Wiechmann, Bad Essen (DE)

(73) Assignee: 3M Innovative Properties Company, St. Paul, MN (US)

(*) Notice: Subject to any disclaimer, the term of this patent is extended or adjusted under 35 U.S.C. 154(b) by 5 days.

This patent is subject to a terminal disclaimer.

(21) Appl. No.: 13/417,907

(22) Filed: Mar. 12, 2012

(65) Prior Publication Data

US 2012/0183917 A1    Jul. 19, 2012

Related U.S. Application Data

(63) Continuation of application No. 12/302,933, filed as application No. PCT/EP2007/055431 on Jun. 1, 2007, now Pat. No. 8,147,243.

(30) Foreign Application Priority Data

Jun. 2, 2006   (DE) .......................... 10 2006 025 845

(51) Int. Cl.  
*A61C 7/00* (2006.01)

(52) U.S. Cl.  
USPC ................................................................ 433/9

(58) Field of Classification Search ............... 433/8, 9, 433/10, 11  
See application file for complete search history.

(56) References Cited

U.S. PATENT DOCUMENTS

| 2,926,422 | A | 3/1960 | Wallshein |
| 3,464,113 | A | 9/1969 | Silverman |
| 4,443,189 | A | 4/1984 | Wildman |
| 4,575,337 | A | 3/1986 | Fujita |
| 4,799,883 | A * | 1/1989 | Stoller et al. ............. 433/17 |
| 4,936,774 | A | 6/1990 | Stoller |
| 5,037,297 | A | 8/1991 | Lerner |
| 5,356,289 | A | 10/1994 | Watanabe |
| 6,264,468 | B1 | 7/2001 | Takemoto |
| 6,582,226 | B2 | 6/2003 | Jordan |
| 7,306,457 | B2 * | 12/2007 | Vigolo ...................... 433/10 |
| 7,354,267 | B2 | 4/2008 | Vogt |
| 8,147,243 | B2 * | 4/2012 | Wiechmann ................ 433/9 |
| 2006/0014116 | A1 | 1/2006 | Maijer |

FOREIGN PATENT DOCUMENTS

| EP | 1 080 697 | 7/2001 |
| JP | 54-109395 | 8/1979 |

* cited by examiner

*Primary Examiner* — Ralph Lewis  
(74) *Attorney, Agent, or Firm* — Philip P. Soo

(57) ABSTRACT

Methods of use are provided, relating to a bracket with a pad for affixing it to a tooth of a patient, with a bracket body that has a slot for receiving an orthodontic wire, and with a channel-like wire guide which has wire guide surfaces for guiding the wire and which is assigned a lateral insertion area for insertion of the wire into the wire guide, wherein the insertion area has, in the longitudinal direction of the wire, a curved section through which the wire can be inserted into the wire guide in an elastically deformed state, such that the wire, on forming back to a rectilinear state, locks in the wire guide, and that the wire guide surfaces enclose the wire in a circle shape, such that the wire is held longitudinally displaceably in the wire guide by the wire guide surfaces and is secured against escaping laterally from the wire guide.

19 Claims, 14 Drawing Sheets

ORTHODONTIC BRACKET WITH A PAD

CROSS-REFERENCE TO RELATED APPLICATIONS

This application is a continuation of U.S. Ser. No. 12/302,933, filed May 5, 2009, now U.S. Pat. No. 8,147,243, which is a national stage filing under 35 U.S.C. 371 of PCT/EP2007/055431, filed Jun. 1, 2007, which claims priority to DE Application No. 102006025845, filed Jun. 2, 2006, the disclosure of which is incorporated by reference in its entirety herein.

The invention relates to a bracket with a pad for affixing it to a tooth of a patient, with a bracket body that has a slot for receiving an orthodontic wire, and with a channel-like wire guide which has wire guide surfaces for guiding the wire and which is assigned a lateral insertion area for insertion of the wire into the wire guide.

PRIOR ART

U.S. Pat. No. 5,037,297 describes a bracket with intersecting slots to receive two orthodontic corrective wires, which exert forces on the bracket body in different directions. The two corrective wires are held by a lock pin so that the two corrective wires can act independently of one another.

Figure 1A:
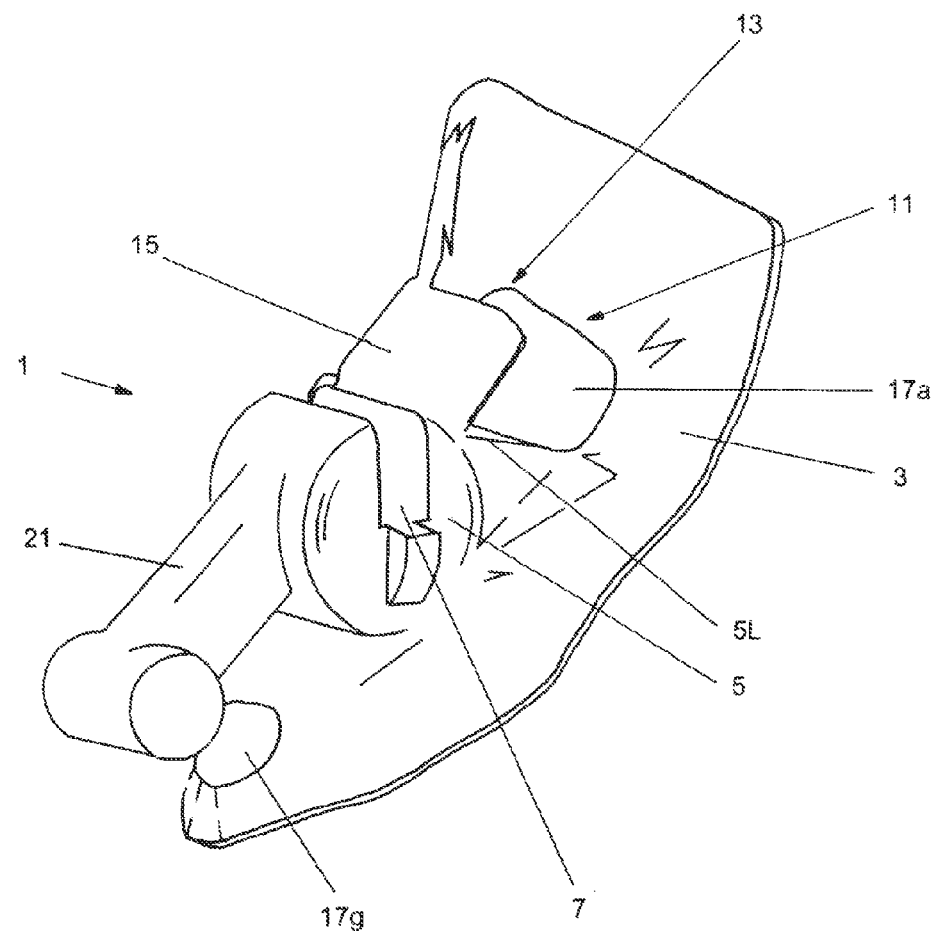
Figure 1A:
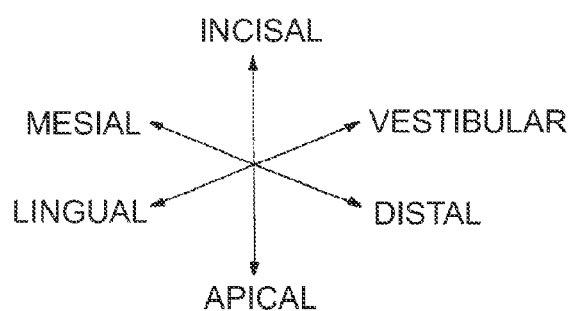

FIGS. 1a), 1b) and 1c) are different views of a known bracket, in which the bracket depicted is a lingual bracket for a lower right front tooth. The bracket 1 comprises a pad 3 and a bracket body 5, in which a slot 7 is formed for receiving an orthodontic wire 9. From the bracket body 5, an occlusal hook 15 extends in the incisal/vestibular direction and a gingival hook 21 in the lingual/apical direction, in which an occlusal groove 17a is assigned to the occlusal hook 15 and a gingival groove 17g to the gingival hook 21.

The hooks 15, 21, which can generally also be called tiewings, serve during the treatment for one thing in the fastening of the orthodontic wire 9 in the slot 7 by means of a ligature or an elastic element, e.g., a rubber band, and for another thing in the fastening of one end of an elastic element, whose other end is fastened to one or more brackets, in order to apply a specific force on the bracket 1 for the translatory movement of the associated tooth.

The gingival groove 17g facilitates the arrangement of the ligature or the elastic element between the gingival hook 21 and the lingual pad surface located opposite it. Furthermore, the free end of the gingival hooks 21 can be arranged closer to the lingual surface of the pad 3 located opposite it by means of the gingival groove 17g.

As an alternative to the arrangement in the slot 7, an orthodontic wire 9 can likewise be arranged between the occlusal groove 17a and the vestibular side of the hook 15. The vestibular or facial surface of the occlusal hook 15, the occlusal groove 17a and a bearing surface 5 L of the bracket body 5 each form in this way a wire guide surface 11F of a channel-like wire guide 11 for the orthodontic wire 9.

In a rectilinear state, the orthodontic wire is easy to guide into the wire guide 11 through an insertion area 13 and to remove from it. In order to hold the orthodontic wire 9 between the wire guide surfaces 11F, it is affixed by means of a ligature or rubber band, which is wound around the gingival hook 21.

The orthodontic wire 9 is often ligated into the wire guide 11 at the beginning of an orthodontic treatment, in order to roughly resolve crowding and overlapping of a patient's teeth. At the beginning of the treatment, the teeth are thus subject to a translation for the greatest part and a rotation only for a small part. For this reason, the relatively imprecise guidance in the wire guide 11, i.e., a form-fitting guide with slackness, is sufficient. To resolve the crowding and overlapping of the teeth, flexible wires are ligated in the wire guide 11, since these are most easily deformed. In this stage of treatment, super-elastic arch wires of 0.012" (0.03048 cm) to 0.016" (0.04064 cm), for example, are preferably used.

Towards the end of the treatment, the teeth are subjected to a translation only for a small part and a rotation for the greatest part, for which reason the orthodontic wire 9 is ligated in the precisely formed slot 7, to reduce the slackness of the orthodontic wire 9 and achieve better control over the movement of the associated tooth. In this stage of treatment, stiffer wires are used, since the teeth are already roughly aligned and these can transmit greater forces and torques to move the teeth. Clinical experience shows, however, that friction, which occurs between the wire guide surfaces 11F and the ligature or rubber band on one side and the orthodontic wire 9 on the other side, has a disadvantageous influence on the duration and the outcome of the treatment.

OBJECT OF THE INVENTION

The object of the present invention is therefore to prepare a bracket, which can also be called an orthodontic support, with a pad, which can also be called a base element, in which the friction arising between the wire guide surfaces 11F and the ligature or rubber band on the one side and orthodontic wire 9 on the other side is reduced.

GENERAL SPECIFICATION OF THE INVENTION

The above-mentioned object is achieved in a bracket according to the invention in which the insertion area of a general bracket has a curved section in the longitudinal direction of the wire through which the wire can be inserted into the wire guide in an elastically deformed state, such that the wire, upon forming back to a rectilinear state, locks in the wire guide, and that the wire guide surfaces enclose the wire in a circle shape, such that the wire is held in a longitudinally displaceable manner in the wire guide by the wire guide surfaces and is secured against escaping laterally from the wire guide.

In one exemplary embodiment, the wire guide can have three wire guide surfaces circularly offset with respect to the wire.

In this case, the bracket advantageously has an occlusal hook with a widened head, so that one wire guide surface is formed by a lingual pad surface, one by a vestibular hook surface and one by an apical surface of the head.

Furthermore, in this case the insertion area preferably comprises an occlusal groove, which is formed in the pad opposite the head.

The insertion area in this case comprises the occlusal groove and a free space between a vestibular surface of the head and the lingual pad surface located opposite it.

The wire guide surface of the head is advantageously formed straight, bent inward or bent outward.

Radially with respect to the wire, the apical surface of the head advantageously has a distance from the lingual pad surface and the vestibular hook surface which is somewhat greater than a diameter of the wire, so that it can be moved in the apical-incisal direction in the wire guide.

In a further exemplary embodiment, the wire guide has four wire guide surfaces circularly offset with respect to the wire.

In this case, the pad advantageously has two pegs sitting opposite one another in the longitudinal direction of the wire and extending lingually, each of which forms a wire guide surface.

Advantageously in this case, the pegs are essentially cylindrical in shape.

The wire guide surface of the pegs is advantageously formed bent outward or straight.

The pegs are advantageously arranged at the same height in the apical direction and sit on the same side of the wire, forming a wire guide surface.

Preferably in this case the further wire guide surfaces are formed by a vestibular surface of an occlusal hook, a bearing surface of the bracket body and a lingual surface of the pad, respectively.

The wire guide surfaces can completely enclose the wire in a circular shape.

Alternatively, the wire guide surfaces can partly enclose the wire in a circle shape.

Furthermore, brackets according to the invention can consist of a pad, a bracket body with the wire guide surfaces according to the invention and at least one or two hooks.

The wire guide surfaces or the slot exhibiting them are preferably formed integrally and/or in one piece with the bracket body. All components of the bracket, the pad, one, two or more bracket bodies are each especially preferably formed integrally and/or in one piece with one another, with the wire guide surfaces according to the invention, and optionally with at least one or two hooks. The integral forming of the bracket with these elements according to the invention can occur by means of metal casting methods, laser sintering of precursor materials, e.g., metal powder, or milling from a single piece of material.

DETAILED SPECIFICATION OF THE INVENTION

Figure 1B:
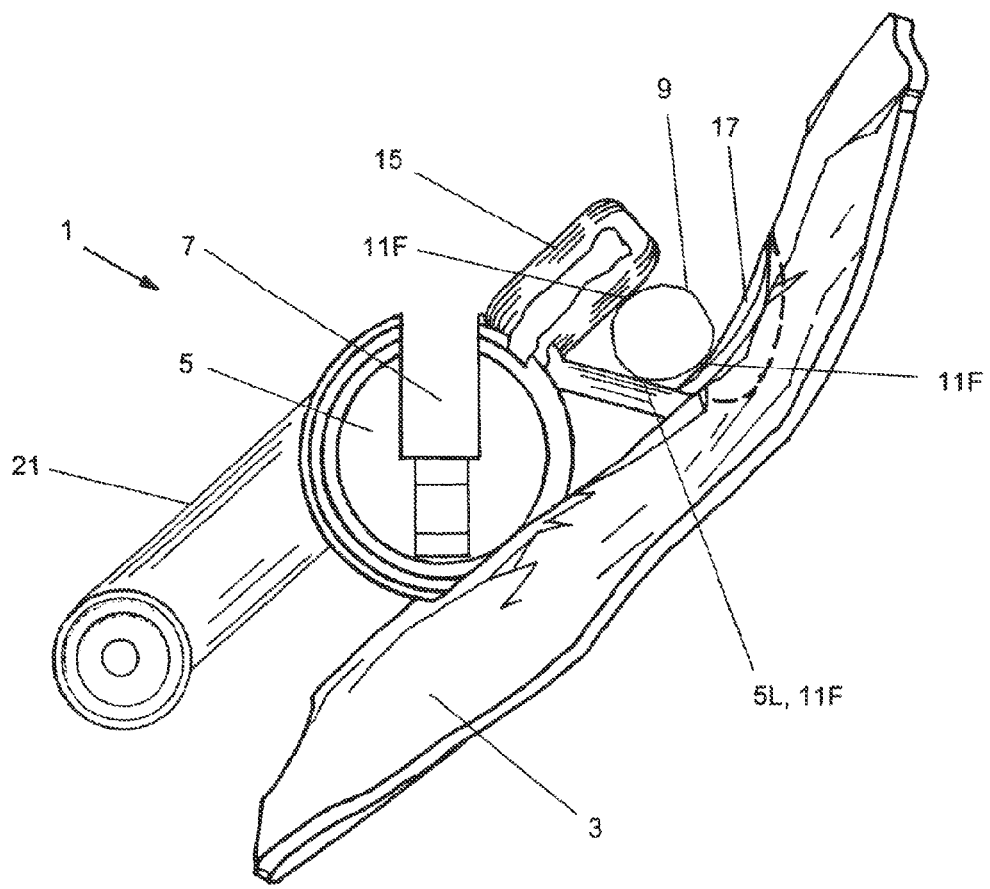
Figure 1C:
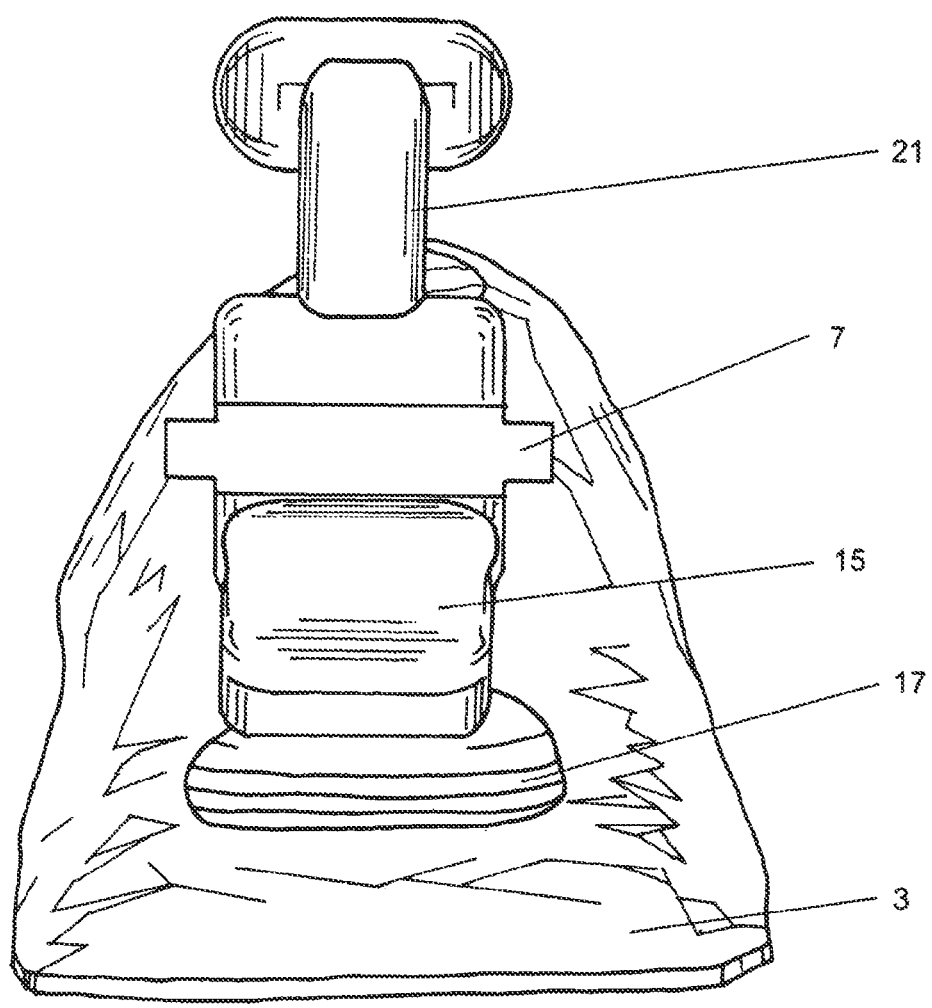
Figure 2A:
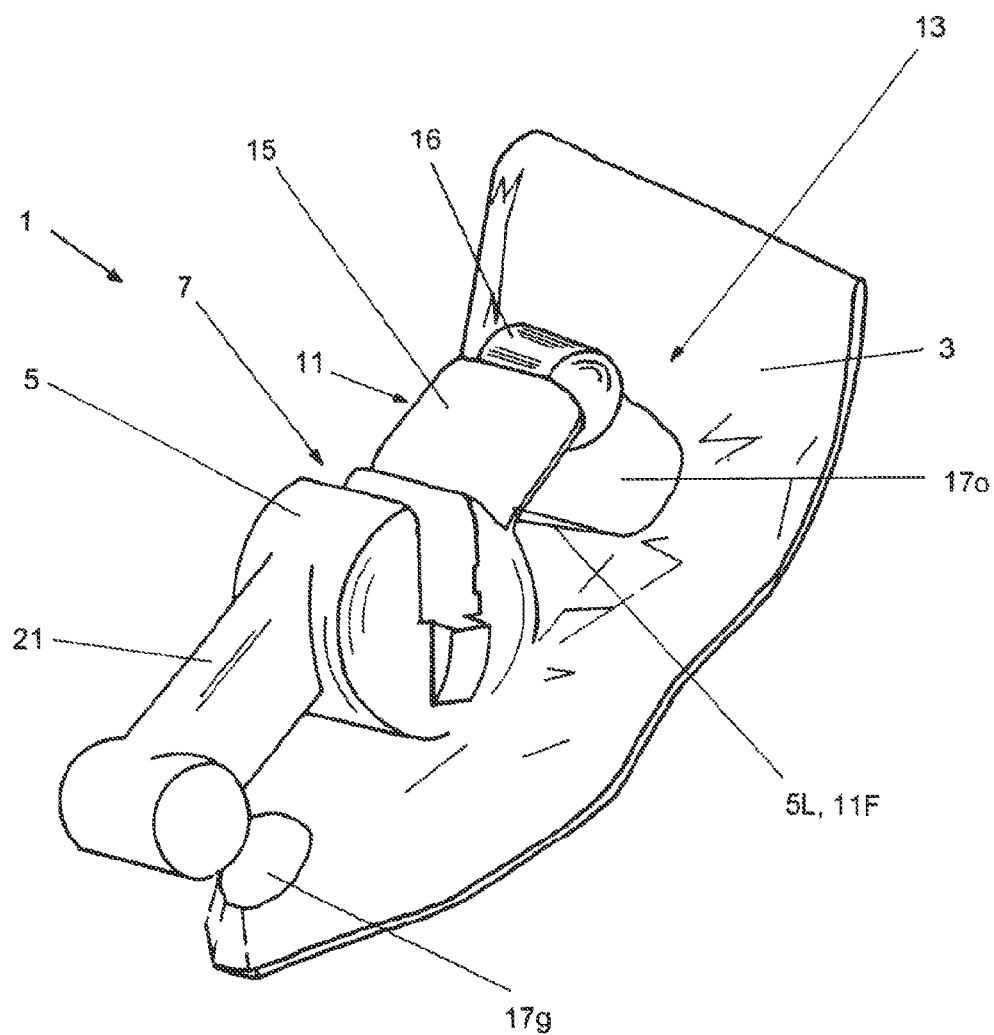
Figure 2B:
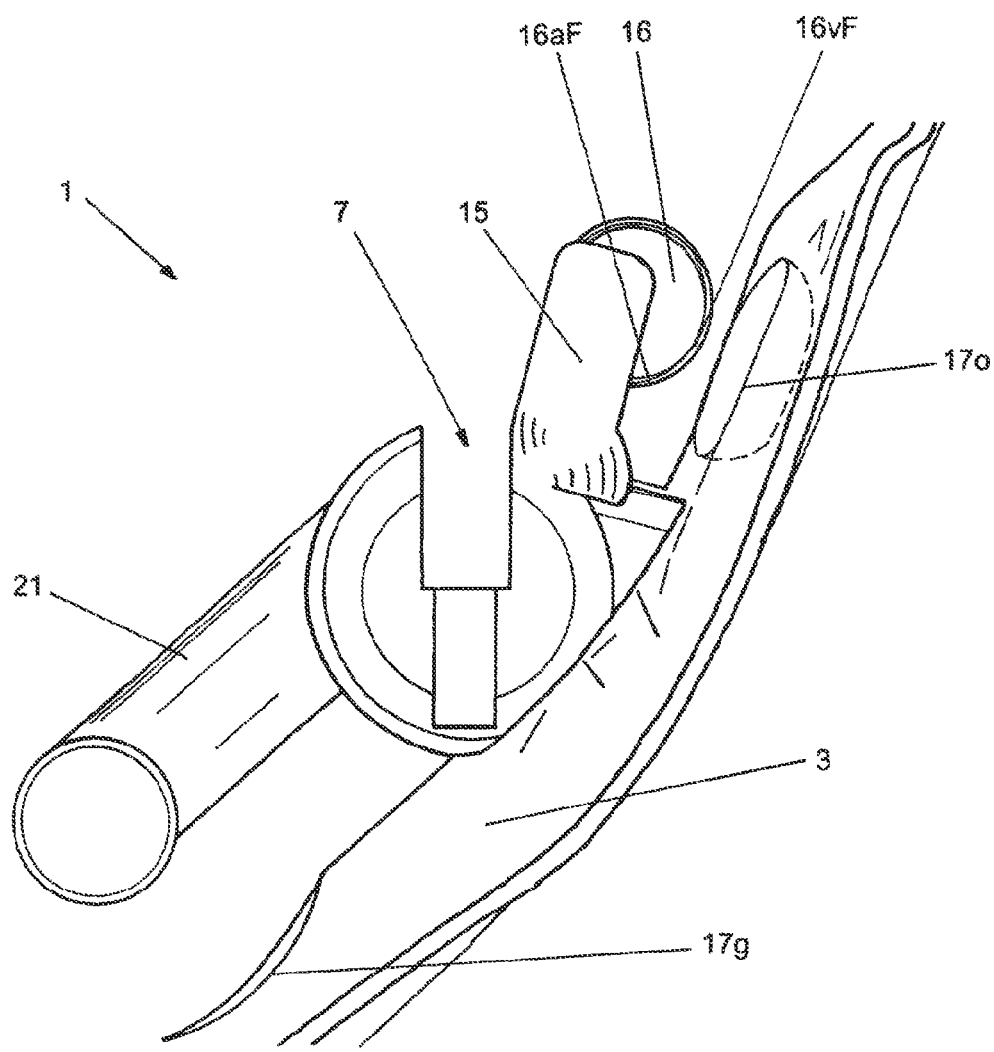
Figure 2C:
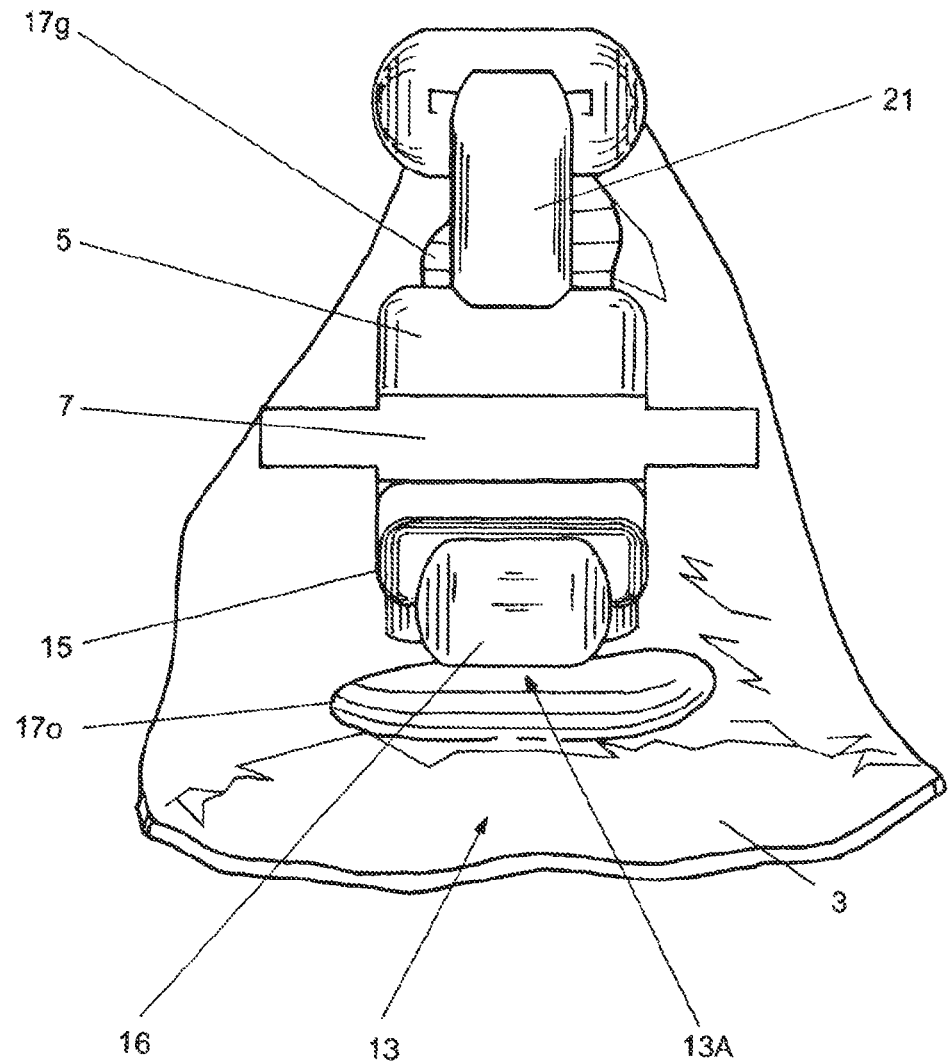
Figure 2D:
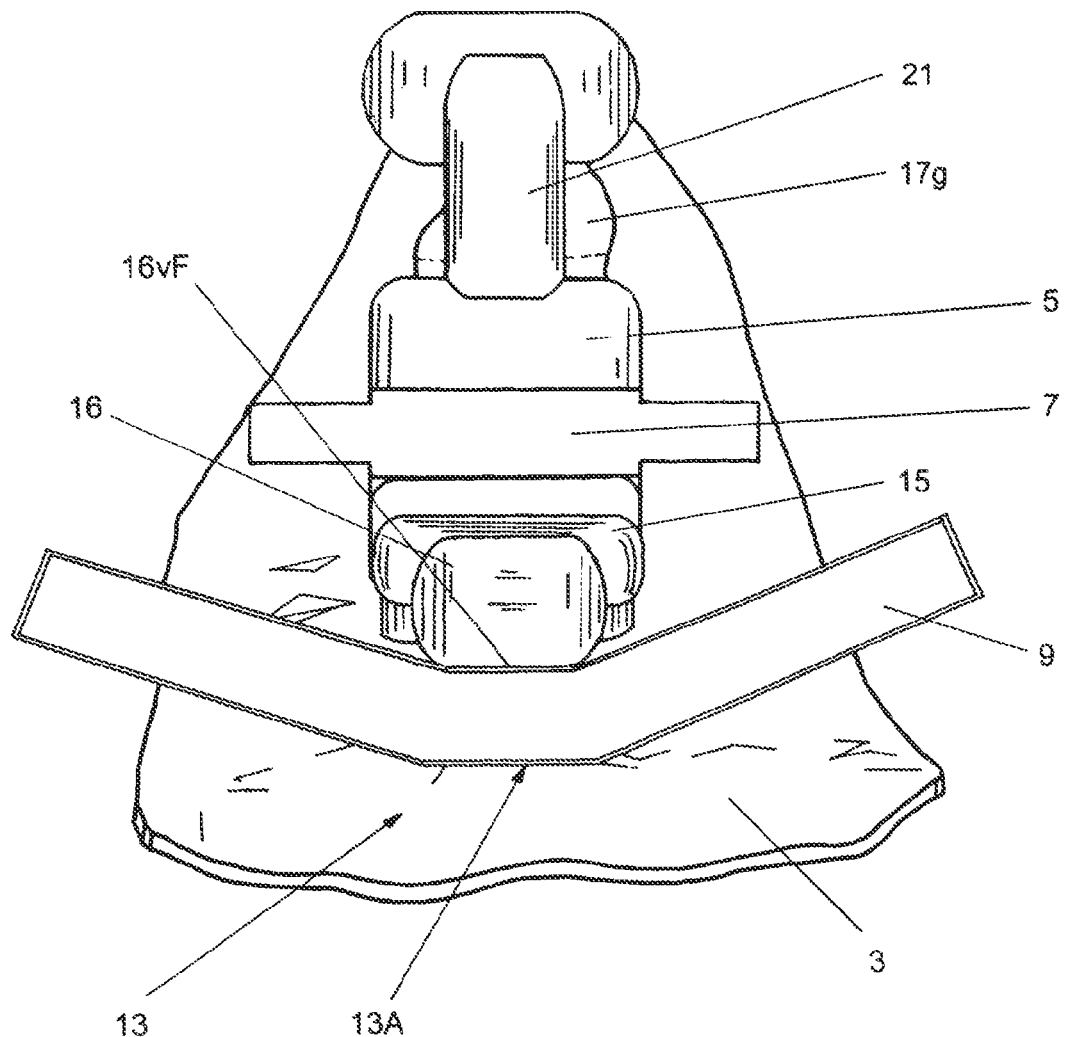
Figure 2E:
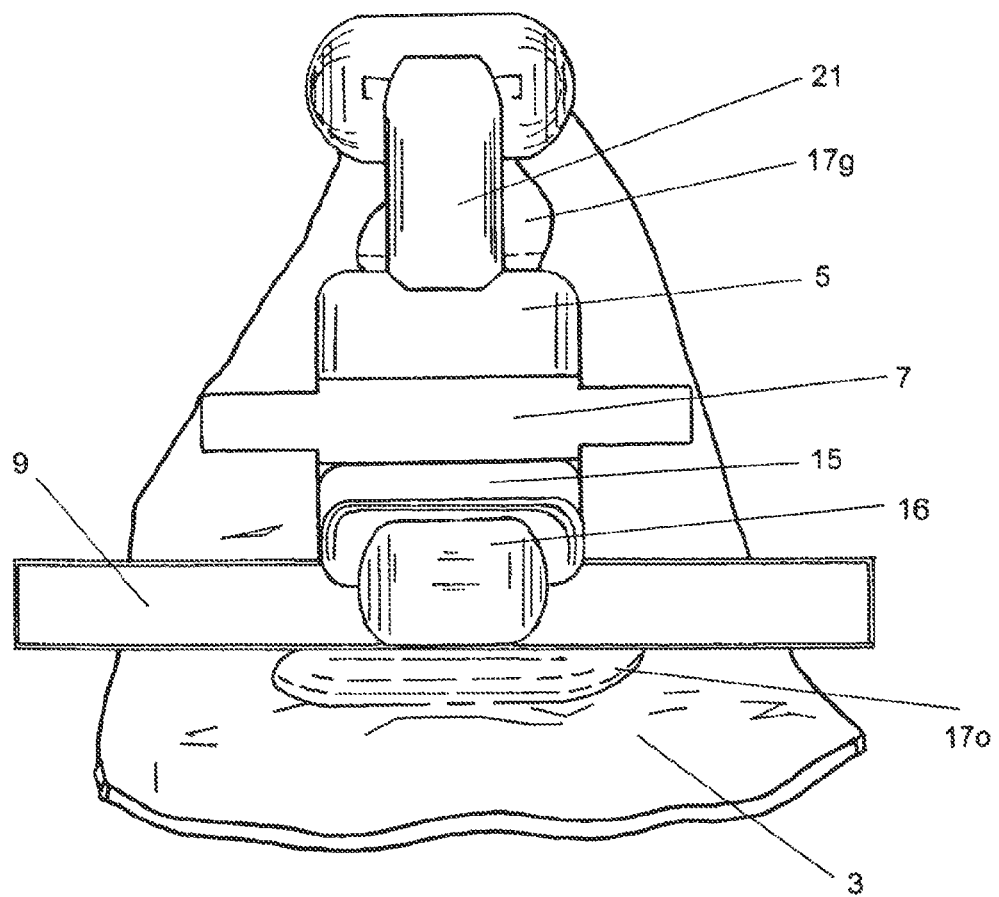
Figure 2F:
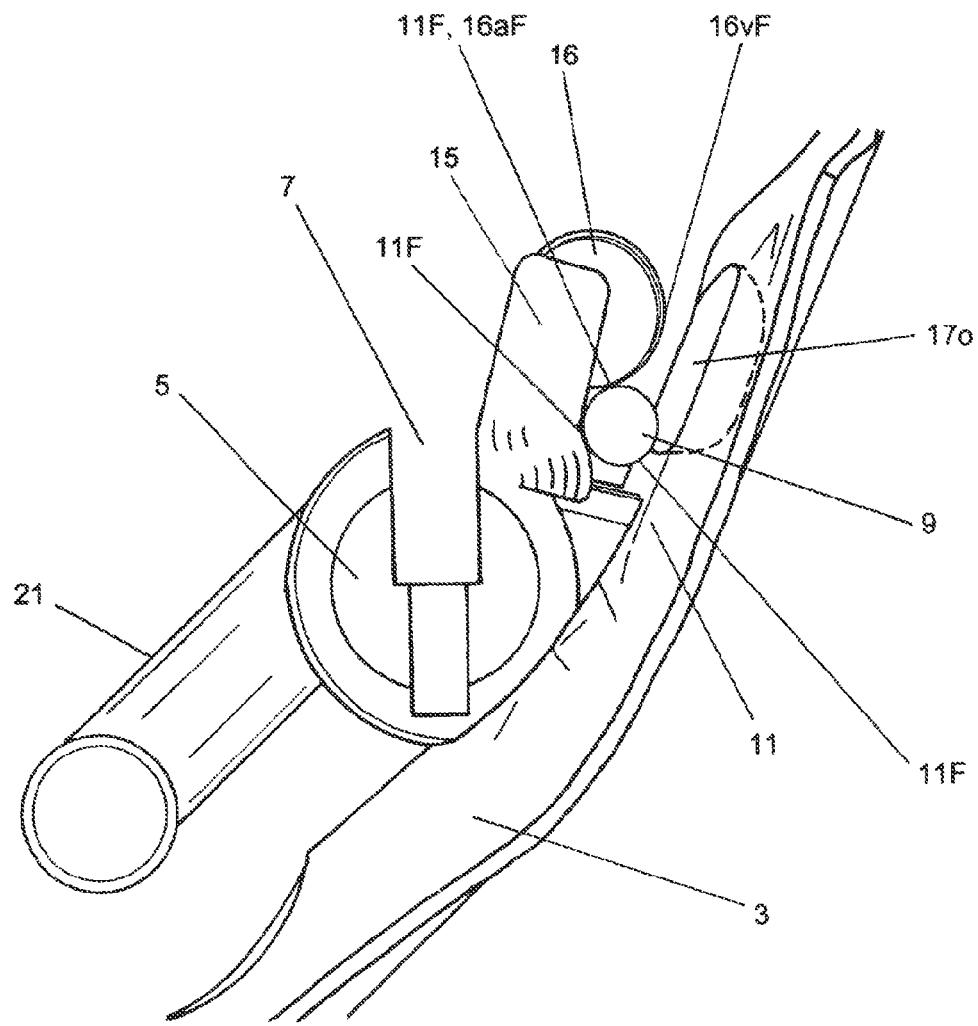
Figure 3:
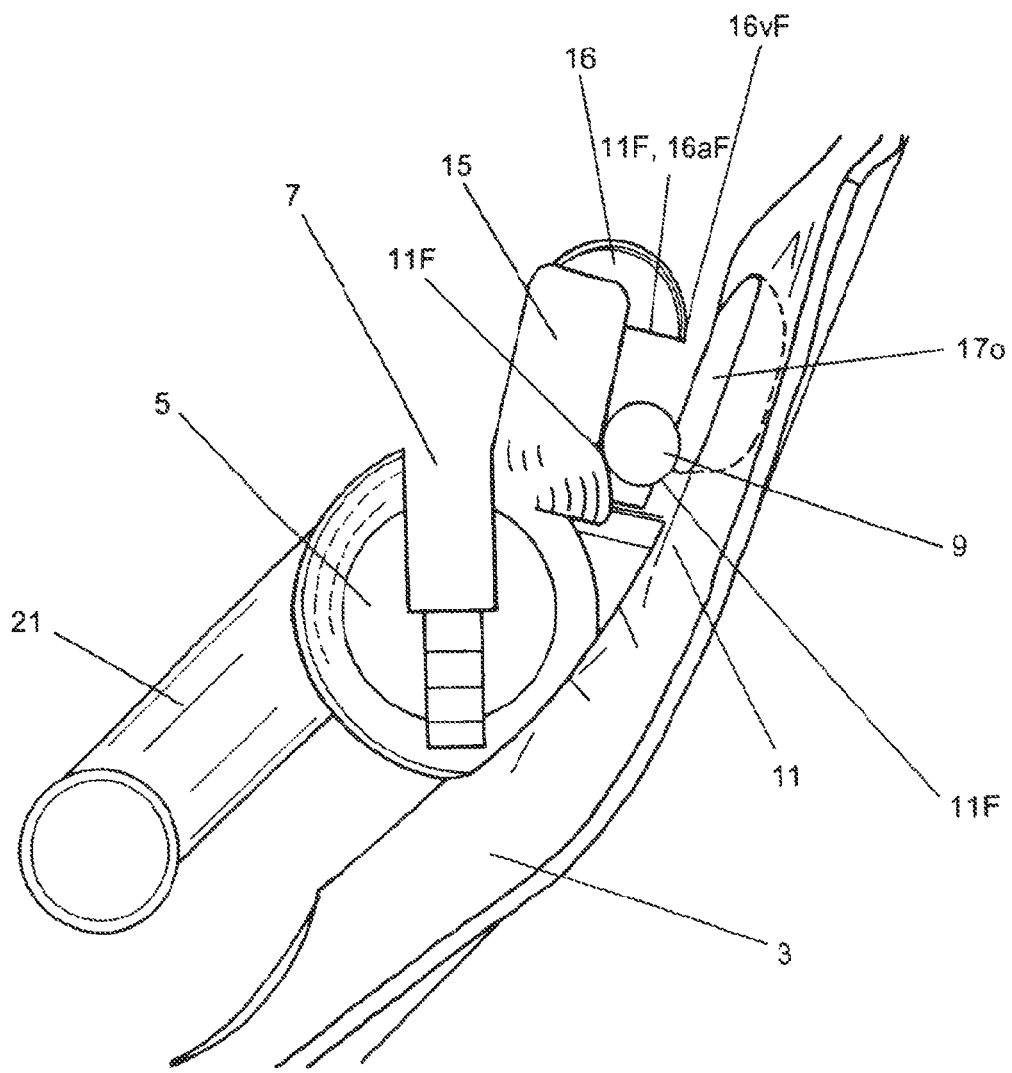
Figure 4:
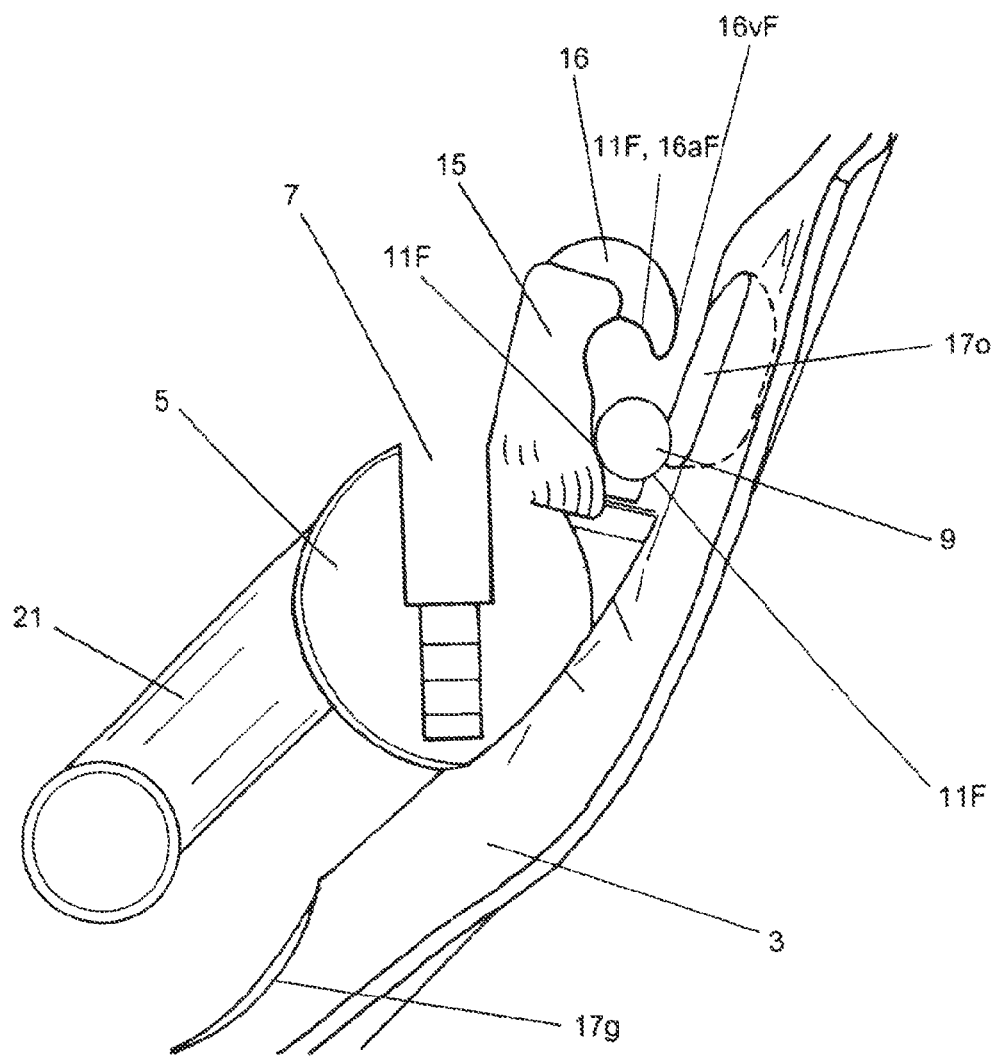
Figure 5A:
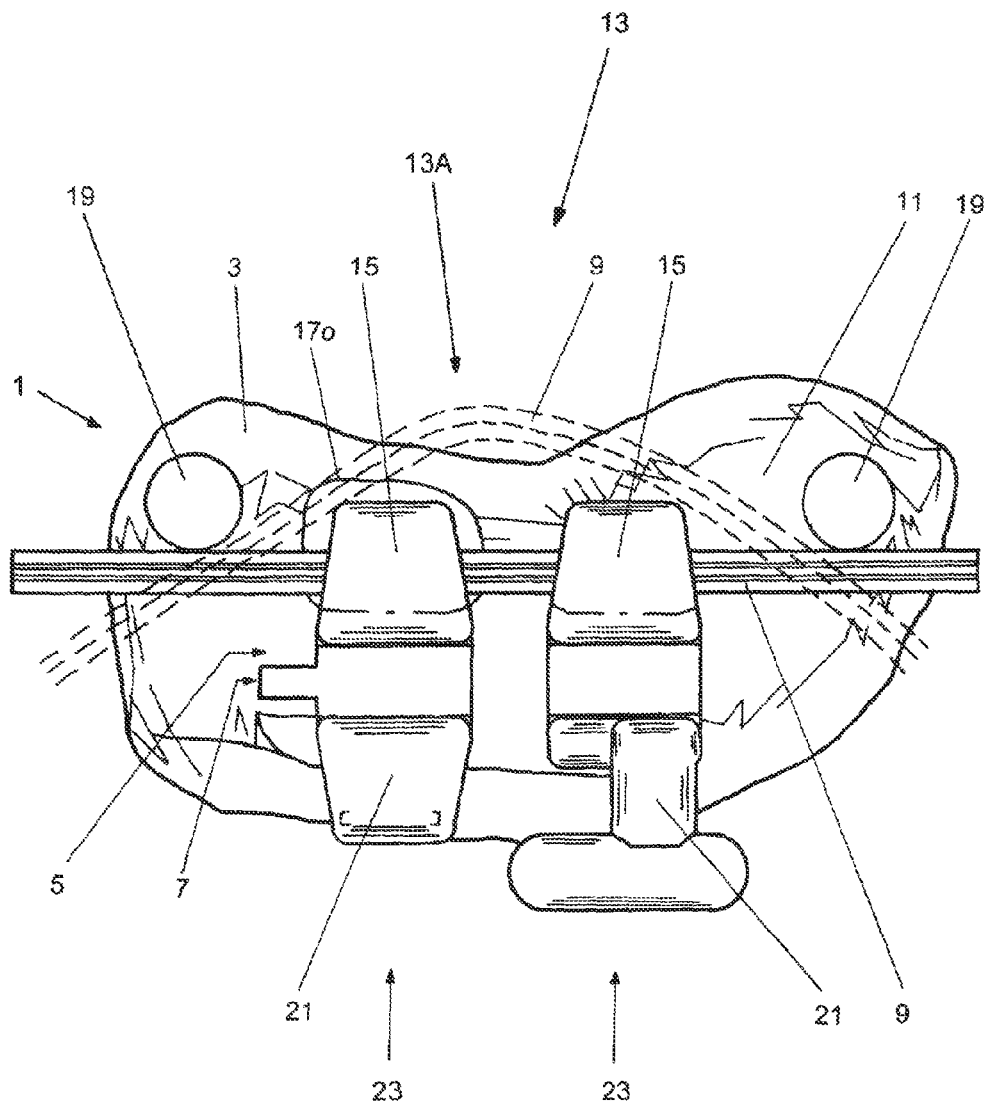
Figure 5B:
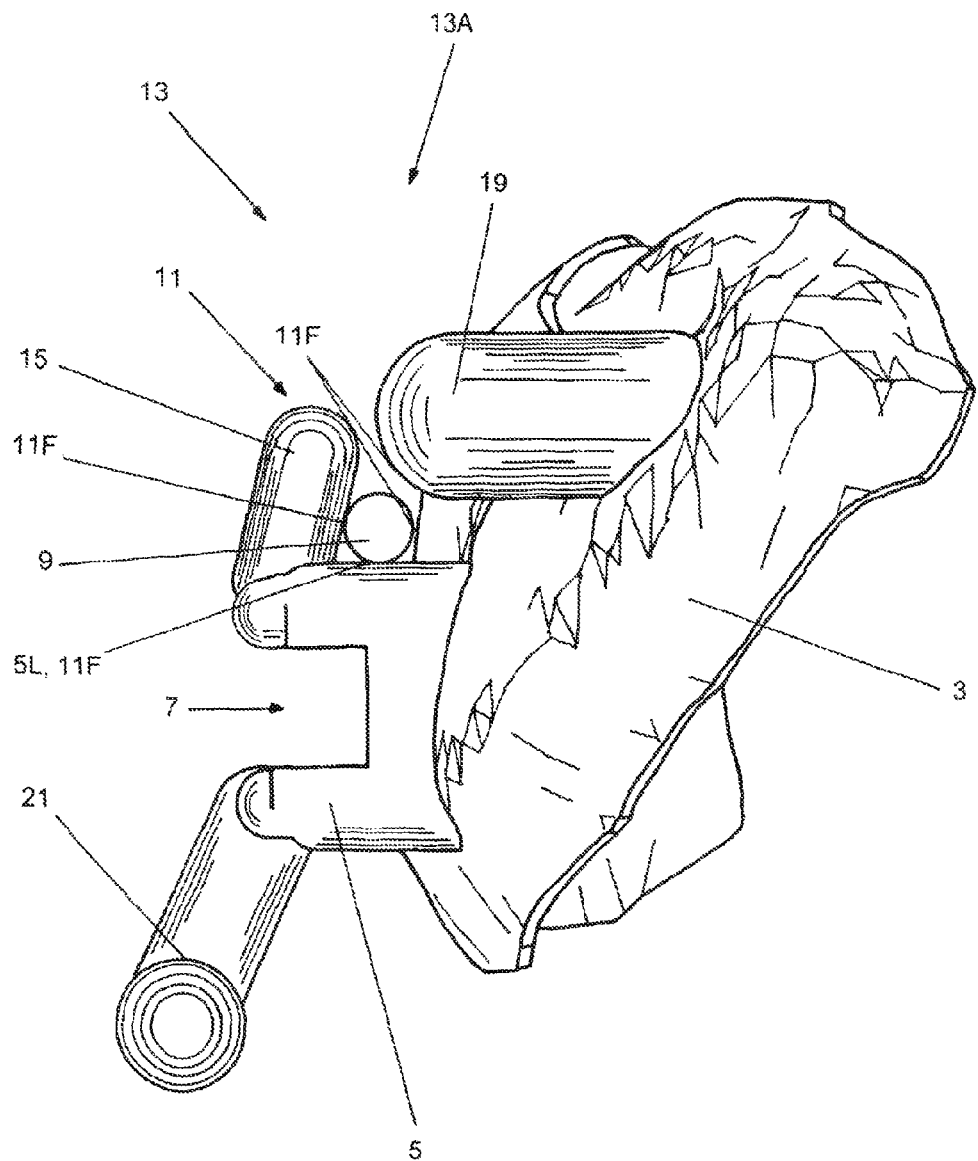
Figure 5C:
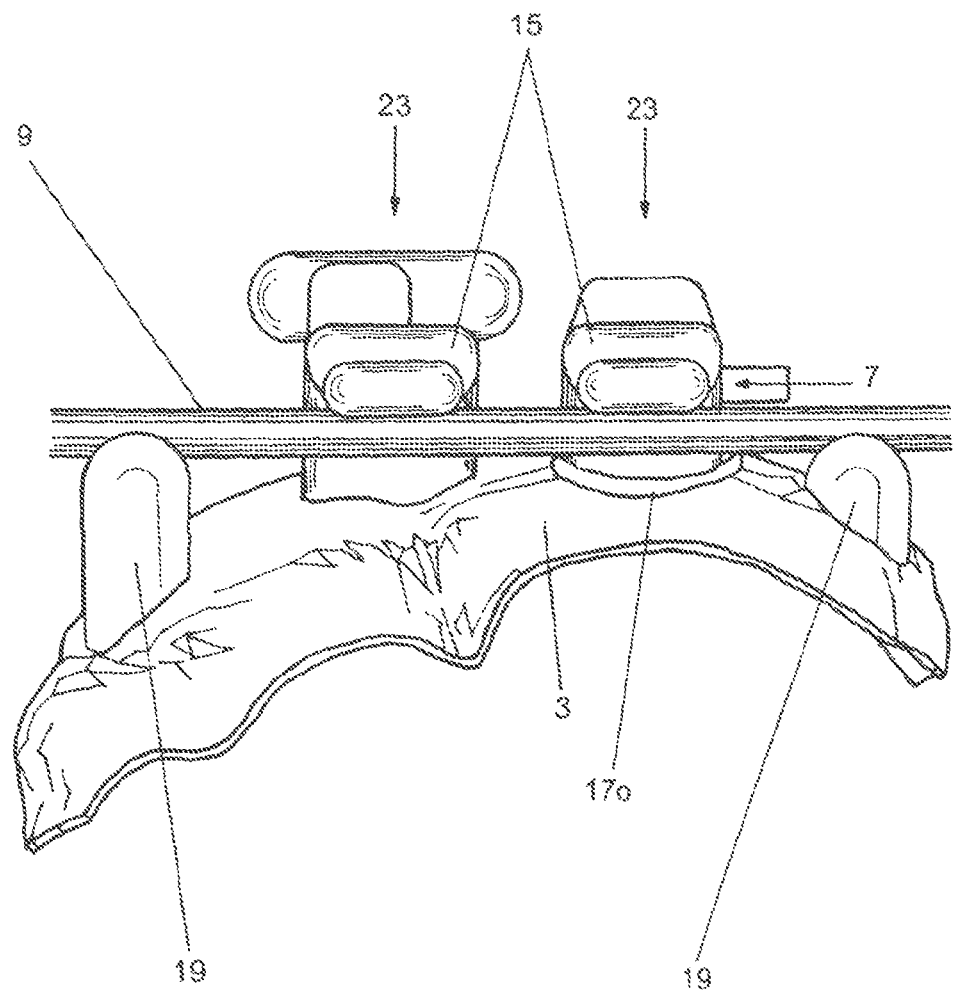

The invention is described below based on two exemplary embodiments with reference to a drawing. In the figures:

FIG. 1a) is a perspective view of a bracket according to the prior art and as a comparative example;

FIG. 1b) is a view of the bracket from FIG. 1a) in the distal-mesial direction;

FIG. 1c) is a view of the bracket from FIG. 1a) in the incisal-apical direction;

FIG. 2a) is a perspective view of a bracket having a wire guide with insertion area according to the invention;

FIG. 2b) is a view of the bracket from FIG. 2a) in the distal-mesial direction;

FIG. 2c) is a view of the bracket from FIG. 2a) in the incisal-apical direction;

FIG. 2d) is a view of the bracket from FIG. 2) in the incisal-apical direction, but with the addition of an orthodontic wire being depicted in the insertion area;

FIG. 2e) is a view of the bracket from FIG. 2a) in the incisal-apical direction, but with the addition of an orthodontic wire being depicted in the wire guide;

FIG. 2f) is a view of the bracket from FIG. 2a) in the distal-mesial direction, but with the addition of an orthodontic wire being depicted in the wire guide;

FIG. 3) is a view of a first variant of the bracket from FIG. 2 in the distal-mesial direction;

FIG. 4) is a view of a second variant of the bracket from FIG. 2 in the distal-mesial direction;

FIG. 5a) is a view of a bracket in the lingual-vestibular direction having a wire guide according to the invention with an insertion area according to a further exemplary embodiment;

FIG. 5b) is a view of the bracket from FIG. 5a) in the mesial-distal direction; and FIG. 5c) is a view of the bracket from FIG. 5a) in the incisal-apical direction.

Referring to FIGS. 2a), 2b) and 2c), the structure of a first exemplary embodiment of a wire guide 11 according to the invention with an insertion area 13 of a bracket 1 is described first.

As described previously for FIG. 1, the bracket 1 in FIG. 2 comprises a pad 3 and a bracket body 5, in which a slot 7 is formed for receiving an orthodontic wire 9. An occlusal hook 15 and a gingival hook 21 are likewise fastened to the bracket body 5. A gingival groove 17g sits opposite the free end of the gingival hook 21 as previously described for FIG. 1.

In addition, however, a head 16 is also formed on the occlusal hook 15, which is essentially cylindrical in shape and runs in the mesial-distal direction. The head 16 projects beyond the vestibular surface of the occlusal hook 15 with a vestibular surface 16vF.

A groove 17o sitting opposite the head 16 in the pad 3 exhibits a contour with such a depth that the mutual distance from the vestibular surface contour of the head 16 and the surface contour of the groove 17o in the lingual-vestibular direction corresponds at least to a diameter of an orthodontic wire 9 to be ligated in, so that it can be arranged between these, but only in a curved, elastically deformed state.

Wire guide surfaces 11F of the wire guide 11 to guide the orthodontic wire 9 are formed from an apical surface 16aF of the head 16, a lingual surface of the pad 3 and a vestibular surface of the occlusal hook 15 as depicted in FIG. 2f). Alternatively, a bearing surface 5L of the bracket body 5 can additionally form a wire guide surface 11F if it has a corresponding width (lingual-vestibular).

An insertion area 13 for the insertion of the orthodontic wire 9 in the wire guide 11 thus has a section 13A in which the wire 9 (around the head 16 and in the groove 17o) must be curved, preventing the insertion of the wire 9 in the wire guide 11 and a lateral escape of the wire 9 from the enclosure by the wire guide surfaces 11F in a rectilinear state. The curved section 13A of the insertion area 13, in which the wire 9 is curved, presently comprises a free space between the head 16 and the groove 17o.

Referring to FIGS. 2d), 2e) and 2f), the insertion of an orthodontic wire 9 into the wire guide 11 is described below.

Starting from a rectilinear state, the orthodontic wire 9 is curved around the vestibular surface 16vF of the head 16, as depicted in FIG. 2d). The deformation of the wire 9 is so slight that it takes place in an elastic region so that the wire is always in an elastically deformed state. In this elastically deformed state, the wire 9 can be guided through the curved section 13A of the insertion area 13, i.e., through the free space between the head 16 and the groove 17o.

Once the wire has passed through the curved section 13A of the insertion area 13, it deforms back to its rectilinear state due to the intrinsic recovery force, as depicted in FIG. 2e) and f). In this rectilinear state, the wire is arranged between the wire guide surfaces 11F of the wire guide 11, i.e., between the apical surface 16aF of the head 16, the lingual surface of the pad 3 and the vestibular surface of the occlusal hook 15.

The orthodontic wire 9 is partly enclosed in a circular shape by the wire guide surfaces 11F as depicted in FIG. 2f).

The orthodontic wire 9 is held in the wire guide 11 in a longitudinally displaceable manner by the wire guide surfaces 11F. It is further secured against escaping laterally from the wire guide 11, in contrast to the prior art according to FIG. 1.

The orthodontic wire 9 held in the wire guide 11 according to FIG. 2 is thus not held in the wire guide 11 by a ligature or elastic element, but exclusively by the wire guide surfaces 11F. As a result, the force exerted on the orthodontic wire 9 perpendicular to its longitudinal direction is reduced, which significantly reduces the friction as compared to the prior art according to FIG. 1.

In order to remove the orthodontic wire 9 from the wire guide 11, it must again be converted into its curved, elastically deformed state. In this state, it can then be guided past the head 16, i.e., through the free space between the head 16 and the groove 17o. Due to its intrinsic restoring force, the wire 9 then deforms back to its rectilinear state.

Referring to FIG. 3, a variant of this exemplary embodiment is described below.

The head 16 in FIG. 3 has an apical surface 16aF, which is formed straight and forms a wire guide surface 11F. This wire guide surface 11F is arranged at a distance from the two other wire guide surfaces 11F that is greater than a diameter of a typically-used orthodontic wire 9.

Orthodontic wires 9 with a large range of cross section shapes and cross section dimensions can be introduced in the wire guide 11 from FIG. 3.

The insertion and removal of the orthodontic wire 9 into/from the wire guide 11 occurs as described previously for FIG. 2.

Referring to FIG. 4, a further variant of this exemplary embodiment is described below.

The head 16 in this variant has an inward-bent, apical surface 16aF, which likewise serves as a wire guide surface 11. The bending of this surface corresponds essentially to the bending of the orthodontic wire 9 so that the wire 9 can slide into it.

This variant can offer improved guidance compared to the variant in FIG. 3, since the slackness of the wire 9 in the wire guide 11 due to the lingual vestibular boundary is less through the apical surface 16aF of the head 16.

The wire guide 11 from FIG. 4 is optimized to a wire cross section shape, preferably to that with the greatest diameter. There can also, however, be wires 9 with a different cross section shape arranged in the wire guide 11 from FIG. 4.

Referring to FIGS. 5a), 5b) and 5c), a second exemplary embodiment of the present invention is described below based on a bracket 1 for a lower left molar.

The bracket 1 from FIG. 5 has a pad 3 and a bracket body 5 with two wings 23, in which a slot 7 is further formed in this for receiving an orthodontic wire 9. Each wing 23 comprises an occlusal hook 15.

Furthermore, the bracket 1 has two pegs 19 extending from vestibular to lingual, which are arranged offset from one another in the longitudinal direction of the orthodontic wire 9. The pegs 19 have a circular cross section and a semi-spherical free end. They are furthermore arranged at the same height in the apical direction and sit on the same side of the orthodontic wire 9.

As depicted in FIG. 5b), a vestibular surface of the occlusal hooks 15 of the wings 23, a bearing surface 5L of the bracket body 5, a lingual surface of the pad 3 and apical surfaces of the pegs 19 each form a wire guide surface 11F. The wire guide surfaces 11F arranged in this way enclose the wire 9 in a circular shape. The wire 9 is again held in the wire guide 11 in a longitudinally displaceable manner by the wire guide surfaces 11F. Since the wire 9 is enclosed in a circular shape by the wire guide surfaces 11F, it is prevented from escaping laterally from the wire guide 11, as can be seen from FIG. 5b) in particular.

The orthodontic wire 9 cannot be inserted in the wire guide 11 from lingual to vestibular because of the occlusal hooks 15. An insertion area 13 for inserting the orthodontic wire 9 in the wire guide 11 has a section 13A in which the wire 9 (around the occlusal hooks 15) is curved upward, see FIG. 5a). As a result, an insertion of the wire 9 in the wire guide 11 and a lateral escape of the wire 9 from the same in a rectilinear state are prevented. The curved section 13A of the insertion area 13, in which the wire 9 is curved, presently comprises a free space incisal to the occlusal hooks 15 of the wings 23 and apical to the pegs 19.

Referring to FIG. 5a), the insertion of the wire 9 in the wire guide 11 and the removal of the wire 9 from the same is described below.

Starting from a rectilinear state, the wire 9 is curved around the occlusal hooks 15 as depicted with dotted lines in FIG. 5a). In this elastically deformed state, the wire 9 can be guided from lingual to vestibular over the hooks 15 and with the lower ends past and below the pegs 19, as depicted in FIG. 5a).

If the wire 9 hits against the pad 3 during movement in the vestibular direction, the force for the elastic deformation of the wire 9 can be removed and, due to its intrinsic restoration force, the wire 9 forms back to the rectilinear state, which is depicted with the continuous line in FIG. 5a).

In the rectilinear state, the wire 9 is enclosed by the wire guide surfaces 11F, as previously described and depicted in FIG. 5b).

When the wire 9 is to be removed from the wire guide 11, the following is done. First the wire 9 is curved so to that it takes the position depicted with dotted lines in FIG. 5a). The wire 9 is moved lingually from this position until it is arranged lingually to the hooks 15 and the pegs 19. The force is then removed for the deformation of the wire 9, as a result of which it forms back to the rectilinear state due to its intrinsic restoration force.

The wire guide 11 in the embodiments described with reference to FIGS. 2 to 5 is an occlusal wire guide 11, i.e., it is formed with the occlusal hook 15. The wire guide 11 can alternatively be a gingival wire guide 11, i.e., formed with the gingival hook 21. In this case, the gingival hook 21 would have to have a head to which a corresponding groove in the opposite pad is assigned in order to form a wire guide apically beyond the slot 7 corresponding to FIG. 2.

The orthodontic wire 9 can generally have any cross section shape, e.g., circular, elliptical, square or rectangular, in which it is possibly advantageous to adapt the wire guide surfaces 11F according to the cross section shape.

The orthodontic bracket 1 is preferably patient-specific, but can alternatively be a partly or completely premanufactured bracket.

The bracket 1 can be a lingual bracket, as described previously, but can alternatively also be a buccal or labial bracket.

The wire guide surfaces 11F can partly or completely enclose the wire 9 in a circular shape, the latter, for example, by lengthening the pegs 19 in FIG. 5b) lingually.

The orthodontic wires 9 are arranged in the wire guide 11 with slackness, which results from the mutual distance from the wire guide surfaces 11F.

| List of reference numbers: | |
|---|---|
| 1 | bracket |
| 3 | pad |
| 5 | bracket body |
| 5L | bearing surface of the bracket body |
| 7 | slot |
| 9 | wire |
| 11 | wire guide |
| 11F | wire guide surface of the wire guide |
| 13 | insertion area |
| 13A | curved section of the insertion area |
| 15 | occlusal hook |
| 16 | head |
| 16aF | apical surface of the head |
| 16vF | vestibular surface of the head |
| 17o | occlusal groove |
| 17g | gingival groove |
| 19 | Peg |
| 21 | gingival hook |
| 23 | Wing |

The invention claimed is:

1. A method of inserting an orthodontic wire into a bracket including a hook, a widened head joined to the hook, and a wire guide having a plurality of wire guide surfaces, the method comprising:
    elastically deforming the wire from a generally rectilinear state to a curved state;
    guiding the wire through a curved insertion area and into the wire guide; and
    allowing the wire to relax back toward the rectilinear state, whereby the wire is retained in a longitudinally displaceable manner within the wire guide by the plurality of wire guide surfaces that prevent the wire from escaping laterally from the wire guide, the wire guide surfaces including a lingual pad surface, a vestibular surface of the hook, and an apical surface of the head, each circularly offset with respect to the wire when viewed along the longitudinal axis of the wire.

2. The method of claim 1, wherein the hook is a gingival hook and the bracket further comprises a gingival groove located opposite the head.

3. The method of claim 1, wherein the hook is an occlusal hook and the bracket further comprises an occlusal groove located opposite the head.

4. The method of claim 3, wherein the occlusal hook is essentially cylindrical and extends along a generally mesial-distal direction.

5. The method of claim 4, wherein the head projects beyond the vestibular surface of the occlusal hook.

6. The method of claim 3, the wire guide further comprising an insertion area including the occlusal groove and a free space between a vestibular surface of the head and opposing lingual pad surface.

7. The method of claim 1, wherein the wire guide surface of the head is formed straight, bent inward or bent outward.

8. The method of claim 1, wherein the wire is movable along the apical-incisal direction within the wire guide by virtue of the apical surface of the head being arranged at a certain distance from the lingual pad surface and the vestibular hook surface, the certain distance being greater than the diameter of the wire.

9. A method of inserting an orthodontic wire into a bracket having a wire guide, the method comprising:
    elastically deforming the wire from a generally rectilinear state to a curved state;
    guiding the wire through a curved insertion area and into the wire guide, the wire guide comprising at least four wire guide surfaces arranged at discrete locations along the longitudinal direction of the wire; and
    allowing the wire to relax back toward the rectilinear state, whereby the wire is retained in a longitudinally displaceable manner within the wire guide that prevent the wire from escaping laterally from the wire guide, the wire guide surfaces being circularly offset with respect to the wire when viewed along the longitudinal axis of the wire.

10. The method of claim 9, wherein at least some of the wire guide surfaces are provided by a pair of pegs extending lingually from the bracket and offset from each other along the longitudinal direction of the wire.

11. The method of claim 10, wherein the pegs are essentially cylindrical.

12. The method of claim 10, wherein the wire guide surface of at least one of the pegs is bent outward or formed straight.

13. The method of claim 10, wherein the pegs are arranged at the same height in the apical direction and located on the same side of the wire, thereby forming a wire guide surface.

14. The method of claim 13, wherein the bracket comprises a body, an occlusal hook, and a pad, and remaining wire guide surfaces comprise a vestibular surface of an occlusal hook, a bearing surface of the body and a lingual surface of the pad, respectively.

15. A method of inserting an orthodontic wire into a bracket including a body, a hook joined to the body, and a pad joined to the body, the method comprising:
    elastically deforming the wire from a generally rectilinear state to a curved state;
    guiding the wire through a curved insertion area and into a wire guide comprising a plurality of wire guide surfaces including at least a groove surface in the pad and corresponding surface of the hook opposing the groove; and
    allowing the wire to relax back toward the rectilinear state, whereby the wire is retained in a longitudinally displaceable manner within the wire guide while prevented from escaping laterally from the wire guide.

16. The method of claim 15, wherein the hook is an occlusal hook.

17. The method of claim 15, wherein the hook is a gingival hook.

18. The method of claim 16 or 17, wherein the hook comprises a head that opposes the corresponding groove to form the wire guide.

19. The method of claim 15, wherein the distance from the groove surface and the surface of the hook is somewhat greater than a diameter of the wire so that it can be arranged therebetween, but only in a curved, elastically deformed state.

* * * * *

UNITED STATES PATENT AND TRADEMARK OFFICE
CERTIFICATE OF CORRECTION

| | |
|---|---|
| PATENT NO. | : 8,435,032 B2 |
| APPLICATION NO. | : 13/417907 |
| DATED | : May 7, 2013 |
| INVENTOR(S) | : Dirk Weichmann |

It is certified that error appears in the above-identified patent and that said Letters Patent is hereby corrected as shown below:

In the Specification

Column 3
Line 54, delete "FIG. 2)" and insert -- FIG. 2a) --, therefor.

In the Claims

Column 8
Line 52, in Claim 18, delete "correponding" and insert -- corresponding --, therefor.

Signed and Sealed this
Eighth Day of July, 2014

Michelle K. Lee
*Deputy Director of the United States Patent and Trademark Office*